United States Patent [19]
Ishak

[11] Patent Number: 5,942,112
[45] Date of Patent: Aug. 24, 1999

[54] HOLLOW FIBER ULTRADIALYZER APPARATUS

[76] Inventor: Noshi A. Ishak, 87 Spring St., Laconia, N.H. 03246

[21] Appl. No.: 08/953,775

[22] Filed: Oct. 17, 1997

[51] Int. Cl.⁶ .......................... B01D 63/02; B01D 61/18; B01D 61/28; B01D 63/04
[52] U.S. Cl. .................. 210/321.6; 210/321.78; 210/321.79; 210/321.8; 210/321.87; 210/321.88; 210/321.89; 210/434; 210/500.23
[58] Field of Search ............. 210/321.6, 321.78, 210/321.79, 321.8, 321.87, 321.88, 321.89, 434, 500.23; 422/44, 48

[56] References Cited

U.S. PATENT DOCUMENTS

| | | | |
|---|---|---|---|
| 4,289,623 | 9/1981 | Lee | 210/456 |
| 4,451,369 | 5/1984 | Sekino et al. | 210/321.9 |
| 4,657,743 | 4/1987 | Kanno | 210/321.78 |
| 5,015,388 | 5/1991 | Pusineri et al. | 210/434 |

*Primary Examiner*—John Kim
*Attorney, Agent, or Firm*—William B. Ritchie; Michael J. Persson

[57] ABSTRACT

A single housing dual compartment hollow fiber membrane dialyzer for hemodialysis is provided having two coaxially oriented hollow fiber membrane bundles encased within the housing. One of the two compartments within the housing is filled with dialysate. The relative orientations of the membranes and the dialysate simultaneously maximize diffusion, convection and ultrafiltration of fluids, solutes and molecules. During dialyzation, these membranes first separate the blood cells and proteins from the plasma with its toxin solutes and smaller molecules. Then, each blood component is dialyzed separately. Finally, the two components are recombined before being returned to the patient. Since the plasma is not discarded, the need for replacement fluid is substantially reduced or in some cases eliminated.

10 Claims, 4 Drawing Sheets

HOLLOW FIBER ULTRADIALYZER APPARATUS

BACKGROUND OF THE INVENTION

1. Field of the Invention

The invention relates to kidney dialyzers, and more specifically to hollow fiber dialyzers.

2. Description of the Related Art

Each year, a significant number of people worldwide develop kidney problems or kidney failure. A majority of these people require temporary or permanent help with the elimination of dissolved waste in the bloodstream. This elimination must be performed to prevent the development of such conditions as uremia and electrolytic imbalance. When these conditions develop and are left untreated, the bloodstream becomes increasingly toxic, and death can occur within days.

The standard medical treatment to eliminate bloodstream waste is hemodialysis (HD), also called simply dialysis. The hemodialysis machine is composed of two main components: the dialyzer or semipermeable membrane, and the pumps and monitors. Blood flows on one side of the membrane while a physiologic solution, called dialysate, flows on the opposite side. The actual process of hemodialysis occurs across the dialyzer membrane. This process involves the forces of diffusion, convection and ultrafiltration. During diffusion small molecules and toxins diffuse from the blood side of the membrane to the dialysate side to purify the blood. During convection the passage of small molecules and toxins are transported through the membrane. This transportation is caused by the hydrostatic pressure of the blood, even in the absence of dialysate on the other side of the membrane. During ultrafiltration the fluid under hydrostatic pressure from the blood side of the membrane moves to the dialysate side.

There have been many changes in the design and geometry of the dialyzer. These have included the designs of Kolff's rotating drum, Kiil's flat plate, Kolff's twin coil and the disposable flat plate. Dialysis membranes have also undergone significant development, advancing from sausage casing to today's biocompatible membranes. For the last 25 years, the hollow fiber membrane dialyzer, developed by the United States National Institutes of Health, has been the most commonly used design. Pairing this design with membranes possessing various characteristics has fostered the development of different modalities of therapy. These include regular hemodialysis (HD), high efficiency HD, high flux HD, hemofiltration, hemodiafiltration, ultrafiltration and plasmapheresis. While there have been significant changes in membrane materials since the development of the hollow fiber dialyzer, the geometry and design of the dialyzer have remained essentially the same.

The flow of fluids and solutes through a membrane during dialysis shows significantly less resistance when tested in vitro as compared to in vivo measurements using blood. This is partially because some of the proteins in the blood are adsorbed to the membrane surface. These adsorbed proteins form a layer over the dialyzer membrane which causes resistance, counteracting the forces of diffusion, convection and ultrafiltration. The higher the protein content of a solution being filtered, the lower the rate of these three forces are achieved. This is a major factor hindering the development of more efficient dialysis since the clearance of middle-sized molecules and other uremic toxins from blood was slowed.

Hemofiltration and hemodiafiltration are two modalities that are more efficient than hemodialysis in achieving blood purification in a given period of time. Recent clinical studies concluded that patients treated with these therapies fared better than those treated with hemodialysis. However, these modalities are not popular. This is because they are very expensive; they require large amounts of fluid, up to 45 liters, which must be replaced with every treatment. Also, they require the modification or replacement of currently used dialysis machines. This makes a change to these therapies prohibitively expensive to most providers of dialysis therapy.

The main difference between these two modalities and hemodialysis is that they are driven by convective and ultrafiltrative transport, while hemodialysis is driven by diffusive transport. In hemofiltration and hemodiafiltration, the hollow fiber dialyzer is used to achieve maximum ultrafiltration and convection forces. In hemodialysis, the same hollow fiber dialyzer is used to achieve maximum diffusion. The hollow fiber dialyzer in its current form cannot maximize all three forces simultaneously. A dialyzer that will provide for the maximum use of these three forces at the same time is the subject of this invention.

Devices designed for the separation and cleansing of blood have been addressed in the prior art. U.S. Pat. No. 5,284,470, granted to Alex T. Beltz, discloses a wearable, portable, lightweight artificial kidney. This device uses chemical treatment instead of dialysis to purify separated plasma. Also, this device is meant for continuous rather than periodic use. Finally, water removal is provided.

U.S. Pat. No. 3,579,441, granted to Clinton E. Brown, discloses a method of blood purification by ultrafiltration. In this invention, ultrafiltration rather than dialysis is used to perform plasma cleansing. Also, this device is designed for continuous use, not periodic application. Further, after filtration, make-up electrolytes are provided.

U.S. Pat. No. 4,289,623, granted to K. Lee, discloses a hollow fiber dialyzer which dialyzes the plasma-blood combination. No means of separation of plasma from blood cells and proteins is disclosed.

U.S. Pat. No. 5,069,788, granted to J. M. Radovich et al., discloses a multi-pass blood washing and plasma removal device and method. This device separates plasma from whole blood and provides for washing of the plasma-depleted component, but does not wash the plasma component. Also, this invention does not provide for recombination of the components.

U.S. Pat. No. 4,789,473, B. Mathieu et al., discloses a method for obtaining plasma or plasma water. This device uses filtration to remove plasma from whole blood. No provision for dialysis or other cleansing is disclosed. Also, the plasma is not returned to the cellular blood component.

U.S. Pat. No. 4,729,829, granted to R. Duggins, discloses a hollow fiber plasmapheresis module which separates plasma from blood. No method of cleansing or plasma return is disclosed.

U.S. Pat. No. 5,008,012, granted to Haguhara et al., discloses a compact plasma separator and apparatus which also separates plasma from blood. No means for cleansing or plasma return are disclosed.

Nothing in the prior art provides for or suggests an apparatus which separates whole blood, dialyzes each component separately, and then combines the components for return to the patient.

SUMMARY OF THE INVENTION

It is an aspect of the invention to provide a dialyzer apparatus which can separate the plasma fluid component of blood from the cellular component before hemodialysis.

It is still another aspect of the invention to provide a dialyzer apparatus which uses diffusion, ultrafiltration and convection to dialyze the plasma fluid component of blood.

It is still another aspect of the invention to provide a dialyzer apparatus which uses diffusion, ultrafiltration and convection to dialyze the cellular component of blood.

It is still another aspect of the invention to provide a dialyzer apparatus which recombines the dialyzed plasma filtrate with the dialyzed cellular blood component.

It is still another aspect of the invention to provide a dialyzer apparatus which employs dialysis equipment commonly in use.

It is still another aspect of the invention to provide a dialyzer apparatus which enables viewing of the interior functioning of the apparatus during dialysis.

The invention is an apparatus for hemodialysis of blood. The apparatus has a housing. The housing is defined by a substantially translucent barrel. The barrel has an interior cross-section, an upper portion and a lower portion. The upper portion and lower portion of the barrel each have a port. The interior cross-section of the housing has a larger dimension along the lower portion than the upper portion. Two headers, each having an opening, are attached to the barrel, one is attached to the upper portion and the other is attached to the lower portion. Two bundles of coaxially oriented hollow fibers are provided for in the housing. The first bundle runs the length of the entire barrel, while the second bundle, oriented coaxially to the first bundle, runs the length of the lower portion of the barrel. The second bundle also has an exterior cross-section which corresponds to the larger interior of the lower portion of said barrel. The apparatus is also provided with tube sheets which separate: the header of the upper portion and the first bundle of coaxially oriented hollow fibers; the header of the lower portion and both bundles of hollow fibers; and the lower portion of the barrel and the upper portion of the barrel.

DETAILED DESCRIPTION OF THE INVENTION

The concept for this device is derived from the physiology of the kidney, particularly from the process in which the kidney separates the blood cells and proteins from the plasma extract prior to dialyzation, also known as the glomerular filtrate. The separated cells and proteins pass through a zone of higher concentration, and are then diluted with the dialyzed plasma extract. If blood cells or proteins leak into the plasma filtrate then it may limit the purification process within the kidney to the point of kidney failure. The apparatus of the present invention applies the same concepts: first, separation of plasma filtrate from the blood cells and proteins by the use of both ultrafiltrative and convective forces, and second, dialysis of each component separately using diffusive forces in addition to the other two forces. The plasma filtrate is free of proteins and cells; therefore, resistance due to membrane adhesion is minimal. This will increase diffusive, convective and ultrafiltrative forces to approximately the same levels as those of in vitro studies.

Figure 1:
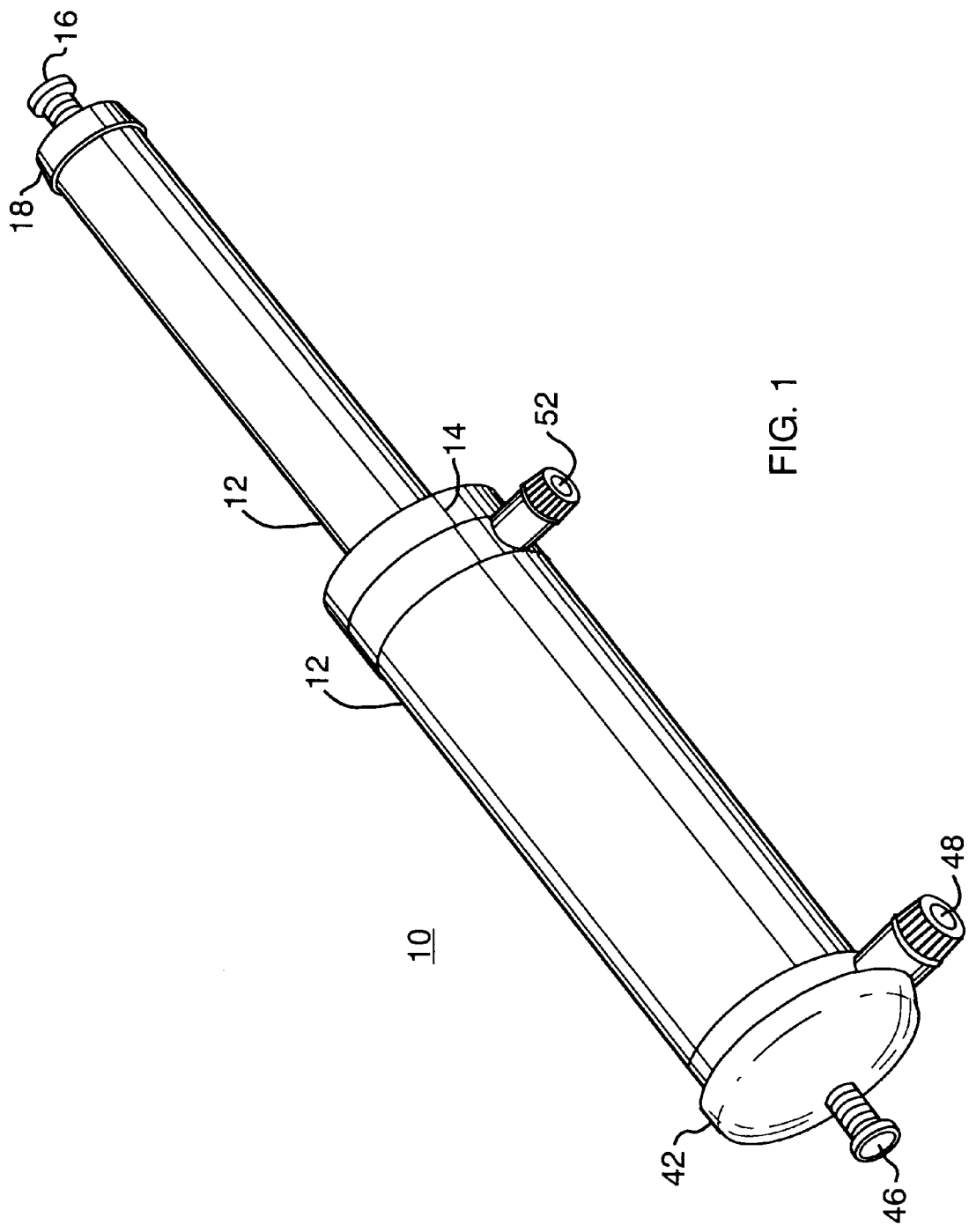
FIG. 1 is an isometric view of the ultradialyzer in accordance with the invention.

Referring now to the drawings, wherein similar reference characters designate corresponding parts throughout the several views, the ultradialyzer apparatus of the present invention is generally illustrated at 10 in FIG. 1. The materials selected for the construction of the invention are preferably plastics of the type well known in the art for constructing similar medical devices. The external shape of the invention, including shell 12, is preferably cylindrical, but other cross-sectional shapes would be acceptable.

The ultradialyzer apparatus is defined by a housing 14. The housing 14 is externally made up of a shell 12, a dialysate inlet port 48, and a dialysate outlet port 52. The diameter of housing 14 and its associated component parts is not critical and can be sized similarly to present dialyzer devices. The shell 12 can be manufactured in a number of ways. However, the most practical, from a cost and quality perspective, is to inject ion mold the unit. The shell 12 may be substantially translucent to permit medical personnel to verify proper internal operation of the device.

The shell 12 has a header at each end . . . an arterial header 18 and venous header 42. Preferably, the headers are removable. Molded into the arterial header 18 is an arterial inlet port 16. Similarly, molded into the venous header 42 is a venous outlet port 46. The arterial inlet port 16 and the venous outlet port 46 communicate with a bundle of hollow-fiber membranes which collectively act primarily as a separation membrane 26 (shown in FIG. 2), although dialysis also occurs in this bundle, particularly in lower section of the apparatus. The arterial inlet port 16 and the venous outlet port 46 are also shaped and dimensioned to match industry standards. The shell 12 also has a dialysate inlet port 48 and a dialysate outlet port 52. Both dialysate ports 48 and 52, communicate with a dialysate compartment 50. The dialysate inlet port 48 and the dialysate outlet port 52 are shaped and dimensioned to match industry standards.

Figure 2:
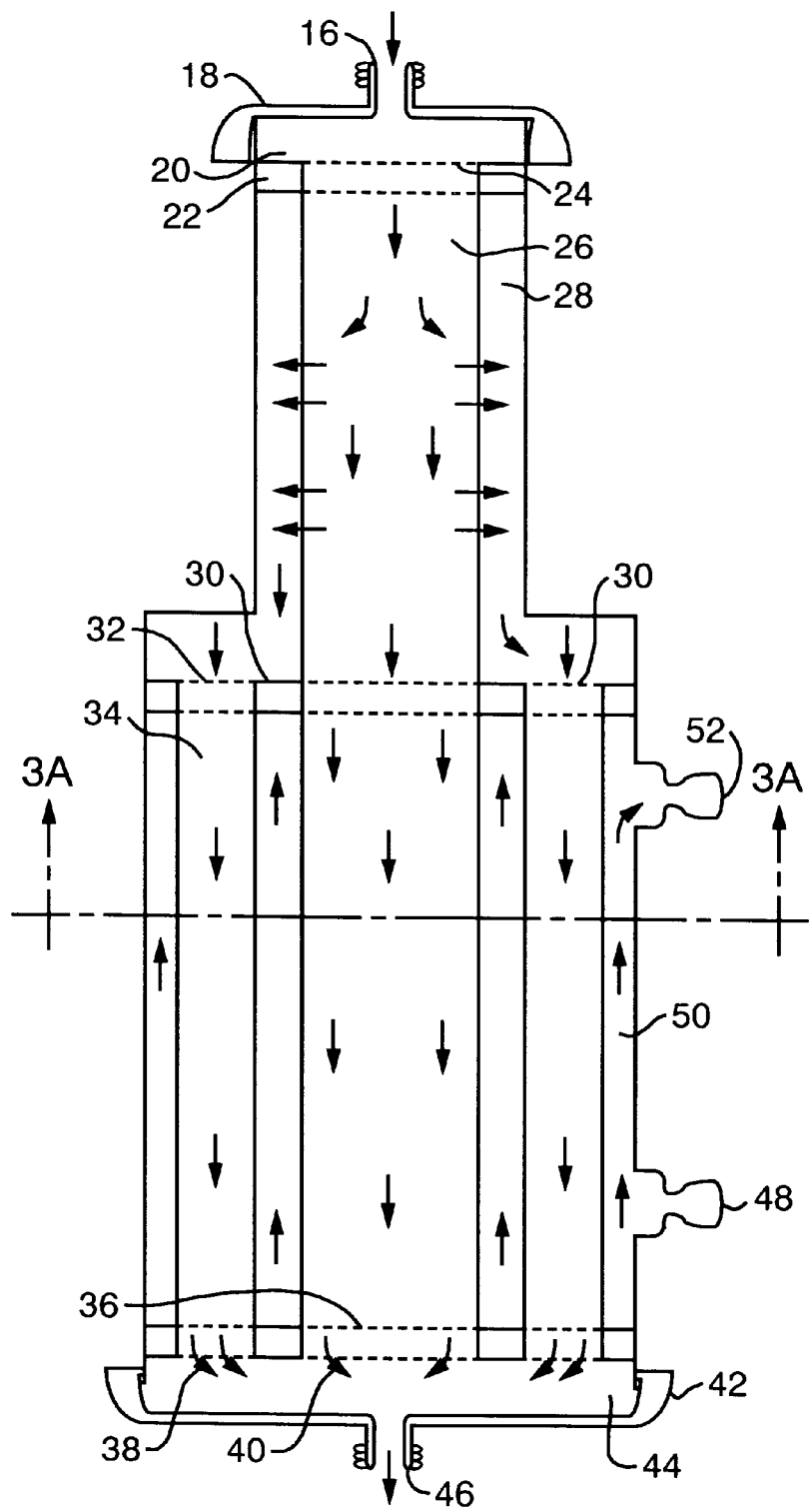
FIG. 2 is a longitudinal side view of the ultradialyzer.

Referring now to FIG. 2, the ultradialyzer apparatus 10 is generally positioned with the arterial header 18 up. The ultradialyzer apparatus 10 should be used with a dialysis machine (not shown) having volumetric control, such as is currently used for high flux dialysis. The dialysis machine should feature standard monitors and alarms in order to ensure a safe treatment. A source of dialysate is connected to the dialysate inlet port 48, while the dialysate outlet port 52 is connected to the outlet dialysate connection of the dialysis machine. A supply of blood to be dialyzed is connected to the arterial inlet port 16 and a blood return is connected to the venous outlet port 46. The blood to be dialyzed enters through the arterial inlet port 16 and proceeds to an arterial blood compartment 20. The arterial blood compartment 20 is the space between the arterial header 18 and an arterial tube sheet 22. All tube sheets are made of any type of potting compound commonly used in the manufacture of dialyzers.

The arterial tube sheet 22 is used to anchor the separation membrane 26 to the shell 12. The arterial tube sheet 22 also acts as a barrier, separating the arterial blood compartment 20 and the ultrafiltrate compartment 28. Blood will then enter the hollow fibers of separation membrane inlet 24 and exit to the separation membrane 26. Preferably, separation membrane 26 extends between both ends of the shell 12 and is supported by the arterial tube sheet 22, a plasma filtrate tube sheet 30 and a venous tube sheet 36. The hollow fibers of the separation membrane 26 pass uninterrupted through these sheets, providing continuous flow of blood without any blockage from one end of the apparatus 10 to the other end. The blood passes at the distal end through a separation membrane outlet 40, where it mixes with the fluid leaving a dialysis membrane outlet 38. This purified blood then passes through the venous outlet port 46 for return to the patient.

Blood passes through the separation membrane 26 between the arterial tube sheet 22 and the plasma filtrate tube sheet 30. Hydrostatic pressure will then cause convective and ultrafiltrative forces to create a plasma filtrate that fills the ultrafiltrate compartment 28. The compartment 28 is dimensioned to achieve an ultrafiltrate of 25–60% by volume of blood infused; the dimension will vary with the membrane characteristics. The membrane length is inversely proportional to its ultrafiltration rate. Compartment 28 volume will be sized differently to achieve different percentages of plasma separation in the range of 25 to 60%. The fluid will contain solutes and molecules of different sizes depending on the nature of the membrane. Also, the protein content of the fluid is negligible or absent, depending on the nature and pore size of the membrane. The ultrafiltrate passes through a dialysis membrane inlet 32 and through a dialysis membrane 34. Next, it passes through a dialysis membrane outlet 38 where it mixes with the blood cells and proteins in a venous blood compartment 44.

The separation membrane 26 and the dialysis membrane 34 comprise a bundle of membrane fibers, typically used for blood dialysis, i.e., standard sizes of polysulphone or cellulose-acetate fibers). The ideal membrane is biocompatible and offers high ultrafiltration, little or no protein leakage, and low clotting. The materials and methods of sterilization and packaging should match current standards. The inlets of the separation membrane 26 and both outlets of dialysis membrane 34 and separation membrane 26 should be flush with the tube sheet potting compound to prevent blood stagnation and clotting.

Explanation of the Changes Affecting the Blood

As blood enters he ultradialyzer apparatus 10, the hydrostatic pressure infusing the blood into the capillaries of the separation membrane 26 creates a convective force. This convective force causes ultrafiltration of solutes and fluids in the plasma. The fluid accumulates in the ultrafiltrate compartment 28, while blood cells and proteins continue downstream to the dialysate compartment 50. At this point, there is a high concentration of proteins in the remaining fluid, creating significant oncotic pressure. This oncotic pressure causes considerable back filtration of the fluid from the dialysate compartment 50 into the separation membrane 26. This back filtration stirs the proteins inside the lumens of the separation membrane 26, disrupting adsorption of the proteins to the membrane surface. Thus, the diffusion process encounters lower resistance than otherwise expected at such a high protein concentration. The back filtration also serves to dilute the concentration of solutes in the plasma, assisting with the diffusive process which is active until the blood reaches the venous blood compartment 44.

The plasma filtrate formed in the ultrafiltrate compartment 28 proceeds through the dialysis membrane 34 within the dialysate compartment 50. Here it is dialyzed more efficiently than it would otherwise be possible since diffusive, ultrafiltrative and convective forces are not obstructed by protein adhesion. Also, the back filtration created in the separation membrane 26 is reflected as additional ultrafiltrative force upon the dialysis membrane 34. Therefore, the plasma ultrafiltrate is subjected to the sum of the combined forces created by back filtration and the negative pressure produced in the dialysate compartment 50 by the dialysis machine pumps. The dialyzed plasma filtrate will then mix with the dialyzed blood in the venous blood compartment 44 for return to the patient.

Figure 3A:
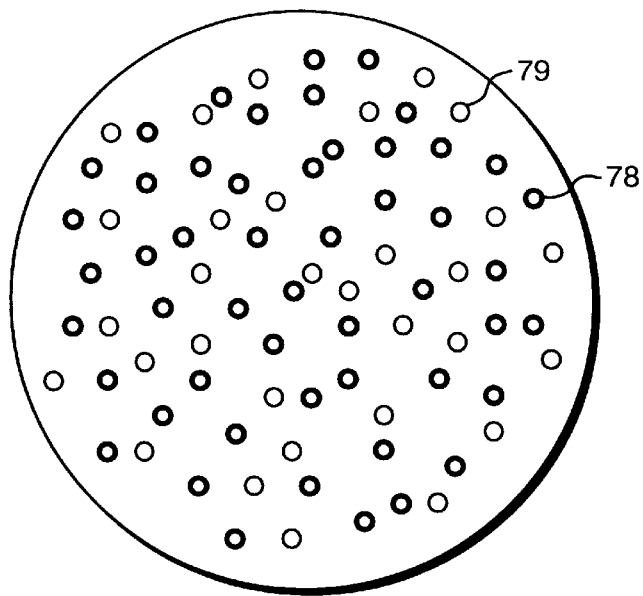
FIG. 3 is an illustration of a side view and a cross-section of the ultradialyzer taken across section line 3—3 showing an alternative embodiment of the hollow fibers.
Figure 3B:
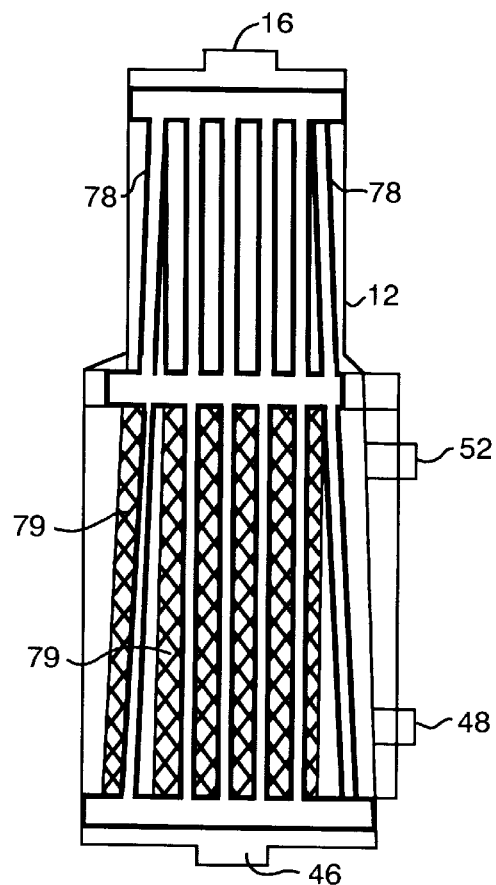

FIG. 3 is an illustration of a side view and a cross-sectional view of the ultradialyzer taken across section line 3—3 showing an alternative arrangement of the hollow fibers 78 and 79. Hollow fibers 78 represent separation membrane 26 and hollows fibers 79 represent dialysis membrane 34. As can be seen, the hollow fibers can arranged in a substantially random fashion, yet provide the advantages described above.

Figure 4:
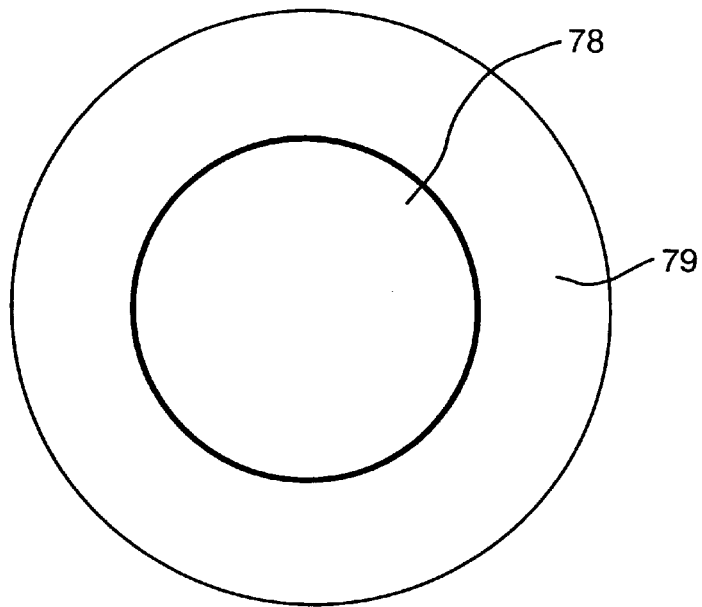
FIG. 4 is an illustration of the cross-section of the invention again taken across section line 3—3 showing the preferred embodiment of the hollow fiber bundles.
Figure 5:
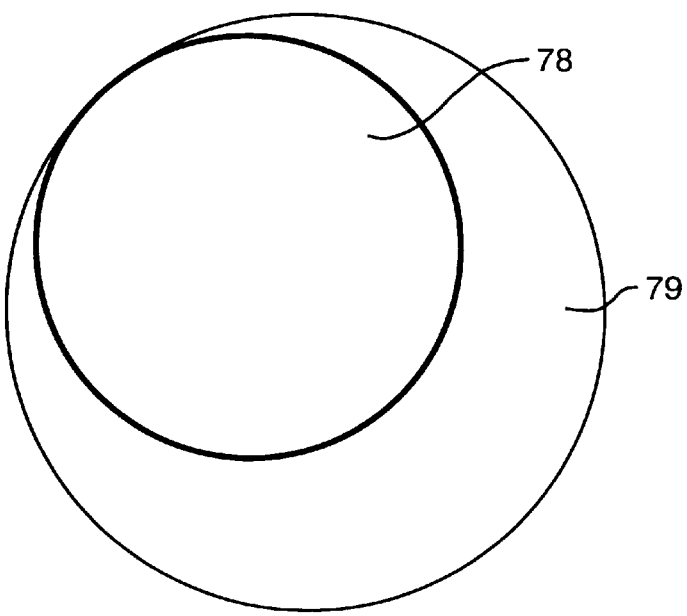
FIG. 5 is an illustration of the cross-section of the invention again taken across section line 3—3 showing another embodiment of the hollow fiber bundle arrangement.

FIG. 4 is an illustration of the cross-section of the invention again taken across section line 3—3 showing the preferred embodiment of the hollow fiber bundles. In this embodiment, hollow fibers 78 again represent separation membrane 26 and hollows fibers 79 again represent dialysis membrane 34. This shows that the first bundle of fibers, that is, separation membrane 26 is preferably surrounded by the second bundle of fibers, that is, dialysis membrane 34. However, as is shown in FIG. 5, an eccentric arrangement of the bundles of fibers could also be used.

While there have been described what are at present considered to be the preferred embodiments of this invention, it will be obvious to those skilled in the art that various changes and modifications may be made therein without departing from the invention and it is, therefore, aimed to cover all such changes and modifications as fall within the true spirit and scope of the invention.

What is claimed is:

1. An apparatus for removing toxins from a patient's blood having a fluid component and a solid component, said apparatus comprising:

a) a substantially translucent shell having an arterial inlet port, a venous outlet port, a dialysate inlet, a dialysate outlet, and an axis, said shell comprising:

an arterial housing having an arterial end, a plasma filtrate exit and a cross-section, wherein said arterial inlet port is adjacent to the arterial end of the arterial housing;

a venous housing having a plasma filtrate entrance, a venous end and a cross section such that the plasma filtrate exit of the arterial housing of said shell is axially connected to the plasma filtrate entrance of the venous housing of said shell, wherein the venous outlet port is adjacent to the venous end of venous housing; and b) a first bundle of co-axially oriented hollow fibers, each of said fibers having an arterial end and a venous end, with said bundle having a cross-section corresponding to the cross-section of the arterial housing of said shell, said first bundle adapted to remove a substantial portion of the fluid component from the solid component of the patient's blood to provide a plasma filtrate and a solid portion, respectively, wherein the arterial ends of each fiber are affixed within the arterial housing, adjacent to the arterial inlet port, and wherein the venous ends of each fiber are affixed within the venous housing, adjacent to the venous outlet port; and c) a second bundle of co-axially oriented hollow fibers, each of said fibers having a plasma filtrate end disposed adjacent to said plasma filtrate entrance of the venous housing and a venous end disposed adjacent to said venous outlet port of said venous housing, with said second bundle having a cross-section such that the cross-section of said second bundle plus the cross-section of said first bundle corresponds to the cross-section of the venous housing, said second bundle being in fluid communication with said dialysate inlet and said dialysate outlet and being adapted to receive a dialysate from said dialysate inlet, to remove a substantial portion of the toxins from the plasma filtrate, and to discharge said dialysate through said dialysate outlet, and wherein the plasma filtrate ends of the fibers are affixed adjacent to the plasma filtrate entrance of the venous housing and wherein the venous ends of the fibers are affixed within the venous housing, adjacent to the venous outlet port of said shell;

wherein the patient's blood is introduced into said apparatus via the arterial inlet port so that the plasma filtrate is separated in the section of said first bundle positioned within the arterial housing such that when the plasma filtrate is provided to said second bundle and when the solid portion is provided to the section of said first bundle positioned within the venous housing, toxins are more easily removed from the plasma filtrate than the solid portion of the patient's blood.

2. The apparatus of claim 1 wherein said dialysate inlet is a dialysate inlet port disposed adjacent to the venous end of said venous housing and wherein said dialysate outlet is a dialysate outlet port disposed adjacent to plasma filtrate entrance of said venous housing.

3. The apparatus of claim 1 wherein said arterial housing further comprises an arterial tube sheet fastened adjacent to the arterial end of said arterial housing, wherein said arterial tube sheet permanently affixes the arterial ends of each fiber of said first bundle together to provide an arterial blood compartment that directs the passage of the patent's blood into said first bundle of fibers.

4. The apparatus of claim 3 wherein said apparatus further comprises an ultrafiltrate compartment positioned within said arterial housing, wherein said ultrafiltrate compartment collects the plasma filtrate provided by said first bundle.

5. The apparatus of claim 4 wherein said venous housing further comprises a plasma filtrate tube sheet fastened adjacent to the plasma filtrate entrance of said venous housing wherein said plasma filtrate tube sheet permanently affixes the plasma filtrate ends of the fibers in said second bundle together so that the plasma filtrate collected in said ultrafiltrate compartment is directed into said second bundle.

6. The apparatus of claim 5 further comprising a dialysate compartment positioned within said venous housing, wherein said dialysate compartment delivers dialysate to the outside of each fiber in said second bundle and that portion of each fiber in said first bundle that is fastened within said venous housing.

7. The apparatus of claim 1 wherein said venous housing further comprises a venous tube sheet fastened, adjacent to the venous end of said venous housing, wherein said venous tube sheet permanently affixes the venous ends of the fibers in both said first and second bundles so that plasma filtrate flowing in said second bundle and the remaining portion of the patient's blood flowing in said first bundle are recombined.

8. The apparatus of claim 1 wherein the portion of fibers of said first bundle that is within said venous housing is randomly distributed within the fibers of said second bundle.

9. The apparatus of claim 1 wherein the portions of fibers of said first bundle within said venous housing are surrounded by and substantially concentric to said second bundle.

10. The apparatus of claim 1 wherein the portions of fibers of said first bundle within said venous housing are surrounded by and eccentric to said second bundle.

* * * * *